US007118668B1

(12) United States Patent
Edelbrock et al.

(10) Patent No.: US 7,118,668 B1
(45) Date of Patent: *Oct. 10, 2006

(54) ELECTROCHEMICAL TEST SENSOR

(75) Inventors: Andrew J. Edelbrock, Granger, IN (US); Matthew K. Musho, York, PA (US); Mark S. Vreeke, Houston, TX (US)

(73) Assignee: Bayer HealthCare LLC, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/978,889

(22) Filed: Nov. 1, 2004

Related U.S. Application Data

(63) Continuation of application No. 10/382,170, filed on Mar. 4, 2003, now abandoned.

(60) Provisional application No. 60/363,380, filed on Mar. 7, 2002.

(51) Int. Cl.
*G01N 27/327* (2006.01)
*G01N 27/333* (2006.01)

(52) U.S. Cl. .............................. 205/777.5; 204/403.04; 204/403.11; 204/403.14; 204/416

(58) Field of Classification Search ................................ 204/403.01–403.14, 416–418; 205/777.5
See application file for complete search history.

(56) References Cited

U.S. PATENT DOCUMENTS

| | | | |
|---|---|---|---|
| 4,935,346 A | 6/1990 | Phillips | |
| 5,049,394 A | 9/1991 | Howard | |
| 5,049,487 A | 9/1991 | Phillips | |
| 5,128,015 A * | 7/1992 | Szuminsky et al. .... | 204/403.05 |
| 5,179,005 A | 1/1993 | Phillips | |
| 5,304,468 A | 4/1994 | Phillips | |
| 5,723,345 A * | 3/1998 | Yamauchi et al. .......... | 436/518 |
| 5,789,255 A | 8/1998 | Yu | |
| 5,798,031 A * | 8/1998 | Charlton et al. ....... | 204/403.14 |
| 6,193,865 B1 * | 2/2001 | Hodges et al. .............. | 204/435 |
| 6,076,645 A1 | 11/2002 | Deng | |
| 6,485,923 B1 | 11/2002 | Yani | |
| 6,531,040 B1 | 3/2003 | Musho | |
| 6,841,052 B1 | 1/2005 | Musho | |
| 2001/0042683 A1 | 11/2001 | Musho et al. ............... | 204/403 |
| 2002/0175075 A1 | 11/2002 | Deng et al. | |
| 2004/0222092 A1 | 11/2004 | Musho et al. | |

FOREIGN PATENT DOCUMENTS

JP HEI1-262470 10/1989

OTHER PUBLICATIONS

Pages 188-189 of Electrochemistry for Chemists, 2nd ed. Sawyer et al., John-Wiley & Sons, Inc. 1995.*
Pegg, D.E., Red Cell Volume in Glycerol/Sodium Chloride/Water Mixtures, Cryobiology 21, 1984, 234-239, MRC Medical Cryobiology Group, University Department of Surgery, Douglas House, Trumpington Road, Cambridge CB2 2AH, United Kingdom.

* cited by examiner

*Primary Examiner*—Alex Noguerola

(57) ABSTRACT

Disclosed is an electrochemical sensor for the determination of analytes in body fluids, e.g. glucose in blood. The sensor involves a non-conductive base which provides a flow path for the body fluid with the base having a working and counter electrode on its surface which are in electrical communication with a detector of current. The base and a cover therefore provide a capillary space containing the electrodes into which the body fluid is drawn by capillary action. The counter electrode has a sub-element which contains an electroactive material and is configured in the system (sensor and meter) to provide an error signal when insufficient body fluid is drawn into the capillary.

30 Claims, 2 Drawing Sheets

ELECTROCHEMICAL TEST SENSOR

CROSS-REFERENCE TO RELATED APPLICATION

This is a continuation application of U.S. Ser. No. 10/382,170, filed Mar. 4, 2003, now abandoned, which claims the benefit of U.S. Provisional Application No. 60/363,380, filed on Mar. 7, 2002, which is incorporated by reference in its entirety.

BACKGROUND OF THE INVENTION

The present invention relates to an electrochemical biosensor which can be used for the determination of analytes such as glucose in blood. Electrochemical biosensors of the type under consideration are disclosed in U.S. Pat. Nos. 5,120,420 and 5,798,031. These devices have an insulating base upon which carbon electrodes are printed and are then covered with a reagent layer comprising a hydrophilic material in combination with an oxidoreductase specific for the analyte. These devices typically involve a base and a cover which are separated by a generally U-shaped piece as a spacer element or, in the case of the '031 patent, use an embossed cover, so that when the base and cover are mated there is created a capillary space containing the electrodes and the reagent layer. A hydrophilic polymer, e.g. carboxymethyl cellulose or poly(ethylene oxide) is used to facilitate the drawing of the aqueous test fluid into the capillary space.

In either embodiment, working and counter electrodes are screen printed onto the base so that an electrochemically created current can flow when these electrodes are electrically connected and a potential is created between them. Touching the opening in the end of the sensor to a drop of test fluid such as blood results in the fluid being drawn into the capillary space, so that it covers the reaction layer on the surface of the electrode. An enzymatic reaction between the oxidoreductase and the analyte creates a flow of electrons which are carried to the working electrode by a mediator such as ferricyanide and flow through the working electrode to a meter which measures the magnitude of the flow. The counter electrode serves dual purposes. First, it provides a fixed potential against which the working electrode is controlled. Second, for a two electrode system, such as that depicted in the drawings, the counter electrode is used to complete the electrical circuit. In this mode, each electron that is transferred to the working electrode is returned to the test fluid at the counter electrode side of the cell. The device's software is programmed to correlate the magnitude of this flow with the concentration of analyte in the test sample. In order for this current to flow, a complete circuit is formed by covering both electrodes with the conductive fluid test sample and applying a potential therebetween.

A problem which is sometimes associated with this type of sensor occurs when an insufficient amount of blood is applied to the opening, so that the working and counter electrodes are not completely covered with the sample. This results in an incomplete current flowing across the electrodes, and, since the amount of analyte detected is directly proportional to the current flowing through the detection meter, failure to completely cover the sensor's electrodes can result in an artificially low reading of the sample's analyte concentration. One technique for dealing with this under filling problem is discussed in U.S. Pat. No. 5,628,890 which involves a mechanism for preventing any response from being detected when the sample volume is too low to provide an accurate reading.

In co-pending application Ser. No. 09/731,943 there is disclosed an electrochemical sensor of the type described above in which a small sub-element of the non-working electrode is positioned upstream from the working electrode, so that when there is insufficient flow of electrical current through the detector to constitute a valid test for the concentration of analyte in the fluid test sample, the pre-programmed detector causes the emission of an error signal to alert the user of the device that the test result should be disregarded. This is achievable because there is generated an altered current profile in the event that the capillary space of the sensor is underfilled. However, in this device, the tripping current carried by the straight carbon sub-element requires some time to reach the necessary potential thereby increasing the duration of the test.

SUMMARY OF THE INVENTION

The present invention is an improvement to an electrochemical sensor for determining the concentration of an analyte in a fluid test sample, e.g. glucose in blood. The sensor comprises:

1) a non-conductive base which provides a flow path for the fluid test sample and has a counter electrode and a working electrode on its upper surface which are in electrical communication with a detector of electrical current;
2) a reaction layer on at least the upper surface of the working electrode comprising an enzyme and a mediator which reacts with the analyte to cause electrons to be transferred between the analyte and the working electrode; and
3) a cover which when mated with the base forms a capillary space with an opening for the introduction of fluid test sample in which the working and counter electrodes are situated within the capillary space so that the major portion of the counter electrode is located downstream of the opening from the working electrode, with a sub-element of the counter electrode being upstream from the working electrode, so that when electrical communication between only the sub-element of the counter electrode and the working electrode takes place, there is insufficient flow of electrical current through the detector to constitute a valid test.

The improvement to the sensor involves the use of a sub-element of the counter electrode which comprises an electroactive material. The electroactive material is sufficiently (electro) positive to allow oxidation to occur at the working electrode under the applied potential and is present in an amount which is insufficient to maintain the flow of electric current through the detector to constitute a valid determination of analyte concentration.

DESCRIPTION OF THE INVENTION

Figure 1:
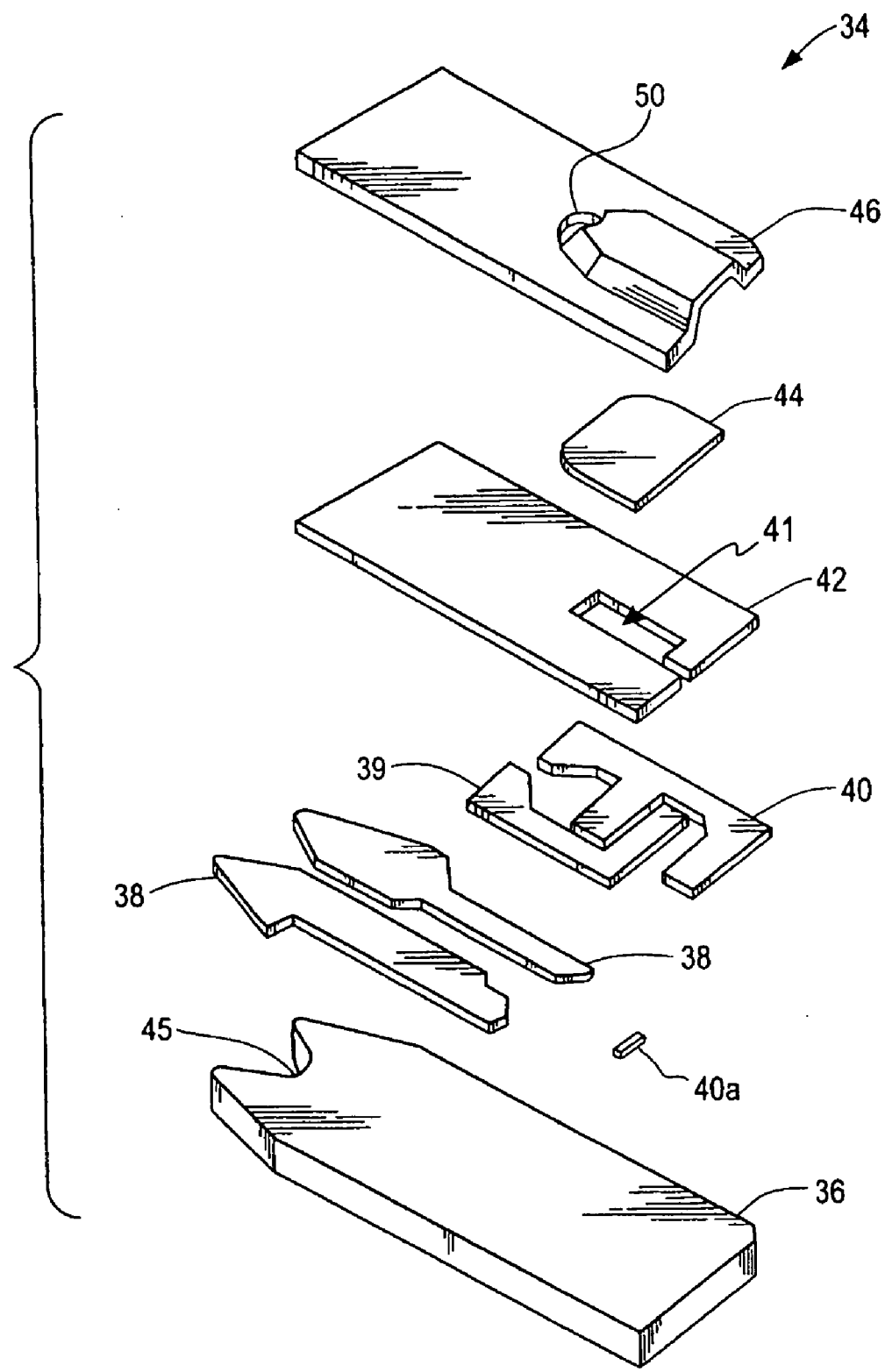
FIG. 1 represents an exploded view of the sensor of the present invention.

The construction of the electrochemical sensor with which the present invention is concerned is illustrated by FIG. 1. Referring to FIG. 1, the sensor of the present invention is made by several printing passes using inks of various compositions. The sensor 34 is made up of insulating base 36 upon which is printed in sequence (typically by screen printing techniques) and counter electrode subunit 40a, an electrical conductive pattern consisting of the conductive leads (38) and the counter electrode sub-element 40A.

In the drawing, this sub-element 40a is a discrete unit, but it could form a continuous trace to the conductive leads (38). The electrode pattern to which 39 is the working electrode and 40 is the counter electrode is produced next. The electrodes are covered with an insulating (dielectric) pattern 42 with a slot 41 to expose the sub-element to the reaction layer 44. The function of the reaction layer is to convert glucose, or other analyte in the fluid test sample, stoichiometrically into a chemical species which is electrochemically measurable in terms of an electrode pattern produced by the components of the electrode pattern. The reaction layer typically contains an enzyme which reacts with the analyte to produce mobile electrons, and an electron acceptor (mediator) such as ferricyanide to carry the mobile electrons to the surface of the working electrode. The enzyme in the reaction layer can be combined with a hydrophillic polymer such as carboxymethylcellulose or poly(ethylene oxide). The two parts, 39 and 40, of the electrode print provide the working 39 and counter 40 electrodes necessary for the electrochemical determination of the analyte which is the crux of the present invention. The working and counter electrodes are configured in a manner such that the major portion of the counter electrode is located downstream (in terms of the direction of the fluid flow along the flow path) from the forward portion of the working electrode 39. This configuration offers the advantage of allowing the test fluid to completely cover the exposed portion of the working electrode for all cases in which an undetected partial fill has occurred. However, sub-element 40a of the counter electrode is positioned upstream from the forward element of the working electrode 39, so that when an inadequate amount of fluid test sample to completely cover the working electrode enters the capillary space, there will be formed an electrical connection between counter electrode sub-element 40a and the exposed portion of the upper part of the working electrode due to the conductivity of the fluid sample, e.g. blood. By programming the current detector to give an error signal when the current profile it receives is below certain pre-determined levels, the sensor system can be designed to actively advise the user that insufficient blood has entered the sensor's cavity and that another test for analyte concentration should be conducted. The system is designed to give an error signal in the case of a short fill by generating a current profile when the capillary space is underfilled which is different from that which is obtained when there is complete filling of the capillary space. However, it was found that this design requires more time than is desirable to activate the assay, which delay may be caused by a lower initial current being generated by the electrodes. It has now been discovered that this delay can be shortened or eliminated by printing the sub-element of the counter electrode with an ink which comprises an electroactive material with the electroactive material being present in an amount which is insufficient to maintain the flow of electrons through the detector to constitute a valid determination of analyte concentration. Conversely, the sub-element is designed to allow a sufficient flow of electrons through the detector to start the timing sequence of the instrument.

The term electroactive material is intended to mean material which is sufficiently positive to allow oxidation to occur at the working electrode under the applied potential. Suitable electroactive materials include AgO or other electropositive metal oxide such as, for example, the oxide of Cu, Mn, Pb, Hg, Ni, Co, Bi, Re or Te or compounds made from these metals. Other classes of electropositive materials which can be used are oxides of metals including those mentioned above and halides of such metals. A metal capable of forming an electropositive metal oxide such as by auto oxidation can be applied to the sub-element of the counter electrode and then oxidized in place to form the metal oxide.

The only requirement of the electropositive material is as stated above. Accordingly, compounds of an electropositive metal such as AgCl can be used since the Ag can be converted to the AgCl species upon contact of the sub-element with a fluid test sample such as plasma or whole blood which contains chloride. This embodiment offers the advantage of not requiring a secondary operation to form the silver oxide layer on the electrode's surface.

The sensor of the present invention is constructed using several screen printing passes using inks of various compositions. The ink for the first pass comprises a material which is of sufficiently low resistance to serve as the conductive leads (38) and contains the electropositive material that forms the sub-element of the counter electrode (40a) as shown in FIG. I. The second pass provides the electrodes 39 and 40 which typically comprise a material incorporating carbon, graphite, palladium or platinum. The electropositive material which can be an oxidizable metal such as one of the metals set out above. As an example, when silver is used, the silver at the surface of the sub-element is oxidized through the curing of the ink or by a secondary oxidizing step. This silver oxide, when contacted with the blood sample which also reaches the working electrode, provides the necessary positive potential to produce the tripping current to start the meter's timing sequence. However, the sub-element (trigger) cannot support the full current generated from the reaction layer which results in the detector determining that the capillary space has not received sufficient test fluid to constitute a valid test.

While the particular dimensions of the electrodes are not critical, the area of the sub-element of the counter electrode is typically less than that of the working electrode. This element is made as small as possible in view of the restraints of the screen printing process. The area which is exposed to the fluid test sample can be made even smaller by printing the dielectric layer 42, so that only a very small portion (2% to 7% of the area of the working electrode) is exposed to provide the sub-element of the counter electrode. In one embodiment, reaction layer 44 can be denied contact with the sub-element 40a of the counter electrode by providing a screen that does not allow printing of reagent ink over the counter electrode sub-element 40a and serves the purpose of starving the sub-element for reagent thereby not allowing it to function as a proper counter electrode. This is preferred, so that an error condition is achieved in the case of failure of the test fluid to contact the bulk of the counter electrode 40.

While sub-element 40a is depicted as being physically disconnected from the rest of the conductive leads (38) in the drawing, it can be physically connected to them forming one continuous path on the counter electrode side. In the embodiment where the sub-element is physically disconnected from the main body of the counter electrode, it is provided with its own connection to the detector through the main body of the counter electrode.

The two parts 39 and 40 of the printed electrodes provide the working and counter electrodes necessary for the electrochemical determination of the analyte. The electrode ink, which is about 14 µm thick, typically contains electrochemically active carbon. Components of the conductor ink are preferably a mixture of carbon and silver which is chosen to provide a path of low electrical resistance between the electrodes and the detector with which they are in operative connection via contact with the conductive pattern at the fish-tail end 45 of the type of sensor depicted in the drawing. The counter electrode can be comprised of silver/silver chloride in which case it will function more like a reference electrode. The function of the dielectric pattern 42 is to insulate the electrodes from the fluid test sample except in a defined area near the center of the electrode patterns to enhance the reproducibility of the detector reading. A defined area is important in this type of electrochemical determination because the measured current is dependent both on the concentration of the analyte and the area of the reaction layer which is exposed to the analyte containing test sample. A typical dielectric layer 42 comprises a UV cured acrylic modified polymethane which is about 10µ thick.

In FIG. 1, the capillary space is formed by mating the embossed lid 46 with base 36 after the various layers have been printed. Outlet 50 serves as a vent for air so that the test fluid can be drawn into the capillary.

The present invention is further illustrated by the following examples:

EXAMPLE I

Metal Converted to Metal Oxide/Metal Halide Construction

The sensor is constructed using various layers of polymer thick film (PTF) to form the working sensor. The conductive leads and trigger subunit is printed from any standard conductive PTF utilizing a metal pigment for high conductivity. In this case, a thermoplastic silver/graphite PTF was used for its cost advantage and cured in an air furnace. The working and counter electrodes were printed using a standard carbon/graphite PTF and the area can be defined using a standard UV or conventional dielectric PTF. The curing of the PTF converts the silver to silver oxide on the PTF surface. Any remaining silver on the surface of the trigger sub-electrode is further converted using an oxygen plasma process that is currently used to improve the performance of the working electrode surface as disclosed in U.S. Pat. No. 5,429,735. This plasma process could also use a halide gas that can react with the metal to form a metal halide at the surface. Alternatively, any wet chemical reaction capable of oxidizing the silver could be used as long as it does not adversely affect the performance of the carbon/graphite electrode. The sensor is then printed with a proprietary reagent PTF to form the working base. The lid is then attached to form the working cell of the sensor.

EXAMPLE II

Metal Oxide Construction

The sensor can be constructed using various layers of PTF's where the trigger PTF has incorporated in it a metal oxide or metal halide. The advantage of this system is that it does not need to be converted to form the necessary electropositive material. In this example, a specialty PTF ink is made using AgO and graphite to form the conductive leads. This ink is screen printed as previously described except that the AgO is not formed during the subsequent air curing or $O_2$ plasma treatment. The electrode and dielectric PTF is printed and cured as in Example I.

Other metal oxides can be used in the manufacture of the PTF, but depending on the conductivity of the oxide it may not function as well for the conducting leads, so that a separate print from the conductive leads would be required. This would increase the cost of manufacturing the sensor due to the need for an additional printing layer.

EXAMPLE III

A base stock, typically of polycarbonate, is printed with various inks to form the electrodes 39 and 40 and then overcoated with a dielectric layer 42 in a predetermined pattern designed to leave a desired surface of the electrode exposed to contact by the fluid test sample as it enters the space formed by mating the lid 46 and the base 36. The particular configuration of the dielectric layer 42 is as depicted in FIG. 1 in which opening 43 leaves the reagent layer in electrical communication with the electrodes 39 and 40 is designed to define the extent to which all of the conductive elements (working, reference and sub-element electrodes) are exposed to the test fluid. Along with the printed conductive features, the dielectric layer defines the size of each of these elements. The electrodes are preferably printed so that the conductive and dielectric layers are close to 90 degrees to each other. This helps in the tolerance stackup for building the sensor because it reduces the registration issues since as either printing shifts around the element, definition remains constant.

Two sensors having trigger electrodes as in FIG. 1, one with a trigger electrode made of carbon and the other comprising Ag/AgO, were prepared as follows:

Carbon Trigger Electrode

A polycarbonate base was printed using DuPont 5085 Ag/graphite conductive PTF ink and cured using either a standard forced air tunnel or an IR tunnel oven to form the conductive leads 38. The electrodes 39, 40 and 40*a* were then printed using DuPont 7102T PTF ink. This ink can be cured using either the forced air tunnel or an IR tunnel oven. A dielectric ink was applied to define the working, reference and trigger electrode area. The sensor was then subjected to an $O_2$ plasma treatment to enhance the electrode surfaces.

Ag/AgO Trigger

In this embodiment, the sensor was produced in the same manner as that with the carbon trigger except that the trigger electrode 40*a* was printed with the Ag/graphite PTF ink along with the conductive leads 38.

The air curing of the DuPont PTF inks (5085 and 7102T) converted the Ag at the surface of the trigger electrode to AgO. The $O_2$ plasma used to enhance the electrode efficiency further oxidized any residual Ag at the surface of the trigger electrode.

These sensors were tested by determining the time required for the counter electrode subunit to reach the tripping current. The meter required that a minimum threshold current be obtained in order to start the timing sequence of the test. In a complete fill situation, the mediator is on the surface of the counter electrode and conversion of the glucose begins immediately to produce a current exceeding the threshold current. In an underfill condition, the mediator is situated several thousandths of an inch away from the trigger electrode. As the conversion of glucose occurs, the mediator must diffuse to the trigger electrode to produce the threshold current needed to start the meter timing sequence. The AgO or other electropositive species has a higher potential than the carbon and, therefore, the time required to render the threshold current is reduced. The trigger electrode is not large enough to carry the full burden of the reaction and is, therefore, not suitable as the counter electrode. The meter is preprogrammed with algorithms which monitor the current profile to detect an underfill condition and give the user an error signal. The result, termed countdown efficiency, was calculated inoculating the sensor with a known volume of blood (1.0 and 1.5 µL in this case) to produce an underfill condition. These volumes, through experimentation, have been determined to partially or fully cover the working electrode. The time required from sample inoculation until the meter starts its countdown was measured as countdown efficiency.

Figure 2:
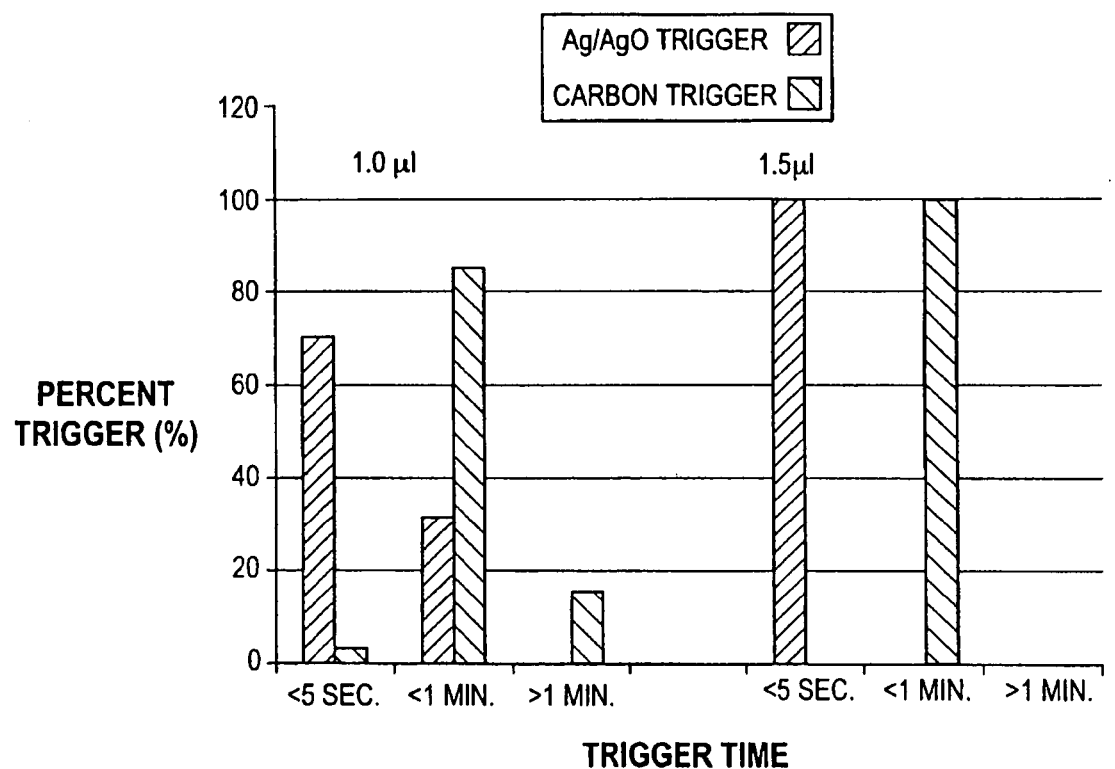
FIG. 2 is a graphical representation of the functionality of a sensor made according to the present invention and one made according to standard techniques.

From the data presented in FIG. 2, it can be determined that the carbon trigger is effective at determining an underfill condition, but the user would have to wait anywhere from 1 second to 3 minutes before the meter would report an error. The present invention was found to decrease the time required for error detection to between 1 second and less than 1 minute depending on the degree of underfill.

For Ag/AgO at 1.0 µL, 70% of the tested sensors tripped immediately and another 30% tripped in less than 1 minute. At 1.5 µL, 100% of the sensors tripped immediately.

For carbon at 1.0 µL, 84% tripped in less than 1 minute and 16% never tripped until the meter errored out at 3 minutes. At 1.5 µL, 100% tripped within 1 minute.

What is claimed is:

1. An electrochemical test sensor for detecting the concentration of an analyte in a fluid test sample, the test sensor comprising:
   a non-conductive base that provides a flow path for the fluid test sample, the base including a counter electrode, a working electrode and a sub-element on an upper surface thereof, the counter and working electrodes being adapted to be in electrical communication with a detector of electrical current, the sub-element being physically disconnected from the counter electrode, the sub-element comprising an electroactive material that is adapted to allow oxidation to occur at the surface of the working electrode under an applied potential;
   a reaction layer on at least the surface of the working electrode, the reaction layer comprising an enzyme; and
   a cover coupled with the non-conductive base and forming a capillary space with an opening for the introduction of the fluid test sample thereto, the space forming a flow path for the fluid test sample,
   wherein the sub-element of the counter electrode is located upstream from the working electrode relative to the opening such that when electrochemical communication occurs between only the sub-element and the working electrode there is insufficient flow of electrical current through a detector to constitute a valid determination of the analyte concentration in the fluid test sample.

2. The test sensor of claim 1 further comprising an insulating layer, the insulating layer exposing a portion of the sub-element to the reaction layer.

3. The test sensor of claim 1 wherein the reaction layer further comprises a mediator.

4. The test sensor of claim 3 wherein the mediator is ferricyanide.

5. The test sensor of claim 1 wherein the reaction layer further comprises poly(ethylene) oxide.

6. The test sensor of claim 1 wherein the enzyme is glucose oxidase.

7. The test sensor of claim 1 wherein the electroactive material is an oxide of Ag, Cu, Mn, Pb, Hg, Ni, Co, Bi, Re, or Te.

8. The test sensor of claim 7 wherein the electroactive material is AgO.

9. The test sensor of claim 1 wherein the electroactive material is a metal halide.

10. The test sensor of claim 1 wherein the cover has a concave portion, the concave portion forming the capillary space when the cover is coupled with the non-conductive base.

11. The test sensor of claim 1 further including a spacer element with a U-shaped indentation, the U-shaped indentation being located between the cover and the non-conductive base and forming the capillary space.

12. The test sensor of claim 1 wherein a major portion of the counter electrode is located downstream relative to the opening and at least a portion of the working electrode.

13. The test sensor of claim 1 wherein the area of the sub-element is less than the area of the working electrode.

14. An electrochemical test sensor adapted to assist in determining the concentration of an analyte in a fluid test sample, the test sensor comprising:
   a base assisting in forming an opening for introducing the fluid test sample;
   a working electrode being coupled to the base;
   a counter electrode being coupled to the base, the counter electrode and the working electrode being adapted to be in electrical communication with a detector of electrical current, a portion of the counter electrode being located downstream relative to the opening and at least a portion of the working electrode; and
   a sub-element being coupled to the base, the sub-element being physically disconnected from the counter electrode, the sub-element comprising an electroactive material that is adapted to allow oxidation to occur at the surface of the working electrode under an applied potential, the sub-element of the counter electrode being located upstream from the working electrode relative to the opening such that when electrochemical communication occurs between only the sub-element and the working electrode there is insufficient flow of electrical current through a detector to constitute a valid determination of the analyte concentration in the fluid test sample.

15. The test sensor of claim 14 further comprising a cover adapted to be coupled to the base to form a capillary space, the capillary space having an opening for introducing the fluid test sample therein, the capillary space forming a flow path for the fluid test sample, the working electrode and the counter electrode being situated in the flow path.

16. The test sensor of claim 15 wherein the cover has a concave portion, the concave portion forming the capillary space when the cover is coupled with the base.

17. The test sensor of claim 15 further including a spacer element with a U-shaped indentation, the U-shaped indentation being located between the cover and the base and forming the capillary space.

18. The test sensor of claim 14 further comprising a reaction layer located on the surface of at least the working electrode, the reaction layer comprising an enzyme adapted to react with the analyte.

19. The test sensor of claim 14 wherein the reaction layer further comprises poly(ethylene) oxide.

20. The test sensor of claim 14 wherein the enzyme is glucose oxidase.

21. The test sensor of claim 14 wherein the electroactive material is an oxide of Ag, Cu, Mn, Pb, Hg, Ni, Co, Bi, Re, or Te.

22. The test sensor of claim 14 wherein the electroactive material is a metal halide.

23. A method of determining whether a sufficient quantity of a fluid test sample has been introduced to an electrochemical test sensor, the method comprising the acts of:

providing the electrochemical test sensor adapted to assist in determining the concentration of an analyte in a fluid test sample, the sensor comprising a base, a working electrode, a counter electrode and a sub-element, the base assisting in forming an opening for introducing the fluid test sample, the working electrode being coupled to the base, the counter electrode being coupled to the base, the counter electrode and the working electrode being adapted to be in electrical communication with a detector of electrical current, at least a portion of the counter electrode being located downstream relative to the opening and at least a portion of the working electrode, the sub-element being coupled to the base, the sub-element being physically disconnected from the counter electrode, the sub-element comprising an electroactive material that is adapted to allow oxidation to occur at the surface of the working electrode under an applied potential, the sub-element of the counter electrode being located upstream from the working electrode relative to the opening such that when electrochemical communication occurs between only the sub-element and the working electrode there is insufficient flow of electrical current through a detector to constitute a valid determination of the analyte concentration in the fluid test sample;

introducing the fluid test sample to the test sensor; and determining whether a sufficient quantity of the fluid test sample has been introduced and, if not, notifying a user that an insufficient quantity of the fluid test sample has been introduced.

24. The method of claim 23, wherein the test sensor further comprises a cover adapted to be coupled to the base to form a capillary space, the capillary space having an opening for introducing the fluid test sample therein, the capillary space forming a flow path for the fluid test sample, the working electrode and the counter electrode being situated in the flow path.

25. The method of claim 24 wherein the cover has a concave portion, the concave portion forming the capillary space when the cover is coupled with the base.

26. The method of claim 24 further including a spacer element with a U-shaped indentation, the U-shaped indentation located between the cover and the base and forming the capillary space.

27. The method of claim 23 wherein the test sensor further comprises a reaction layer located on the surface of at least the working electrode, the reaction layer comprising an enzyme adapted to react with the analyte.

28. The method of claim 23 wherein the electroactive material is an oxide of Ag, Cu, Mn, Pb, Hg, Ni, Co, Bi, Re, or Te.

29. The method of claim 23 wherein the electroactive material is a metal halide.

30. The method of claim 23 wherein the analyte is glucose.

* * * * *